United States Patent [19]

Sehon et al.

[11] Patent Number: 5,358,710
[45] Date of Patent: Oct. 25, 1994

[54] METHOD FOR THE SUPPRESSION OF AN IMMUNE RESPONSE

[76] Inventors: Alec Sehon, 695 Academy Road, Winnipeg, MB, Canada R3N 0E8; Pradip K. Maiti, 80 Lake Village Road, Winnipeg, MB, Canada R3T 4M8; Masaru Takata, 508-571 William Avenue, Winnipeg, MB, Canada R3E 0Z2

[21] Appl. No.: 66,314

[22] Filed: May 24, 1993

Related U.S. Application Data

[63] Continuation of Ser. No. 444,263, Dec. 1, 1989, abandoned.

[51] Int. Cl.$^5$ .................. A61K 39/35; A61K 39/385; A61K 39/44; A61K 39/00
[52] U.S. Cl. ..................... 424/178.1; 424/183.1; 424/280.1; 424/810
[58] Field of Search ................ 424/88, 89, 91, 92, 424/78, 17, 78.18, 78.24, 78.31, 85.91

[56] References Cited

U.S. PATENT DOCUMENTS

| | | | |
|---|---|---|---|
| 4,261,973 | 4/1981 | Lee et al. | 424/78 |
| 4,276,206 | 6/1981 | Katz | 424/78 |
| 4,296,097 | 10/1981 | Lee et al. | 424/78 |
| 4,430,260 | 2/1984 | Lee et al. | 424/78 |

OTHER PUBLICATIONS

Bitoh et al (1993) Cellular Immunol 150: C68–C93.
*Handbook of Experimental Immunology* 2nd edition Ed. D. M. Weir, Blackwell Scientific Publications, Oxford 1973 p. 35.3.
Sehon, A. H., "Down Regulation of IgE Antibodies by Suppressogenic Conjugates" (1983) Academic Press Japan, Inc. pp. 483–491.
Sehon, A. H., "Modulation of Antibody Responses by Conjugates of Antigens with Monomethoxypolyethylene Glycol", from Immunobiology of proteins and Peptides V, Plenum Publishing Corp, (1989) ed. by M. Z. Atassi pp. 341–351.
Sehon, A. H., "Immunological Strategies for Therapeutic Destruction and HIV–Infected Cells in Asymptomatic Patients", MCR Group for Allergy Research. pp. 570–574 Progression Allergy and Clin. Immunology, Proceedings 35th Int.Cong. Aller.
Sehon, A. H., "Potential use of Allergens Modified with Monomethoxypolyethylene Glycol for Immunotherapy of Atopic Patients", pp. 313–319, in the Proc. XII International Congress of Allergology and Clin. Immunol. 1986.

*Primary Examiner*—Kay K. Kim
*Attorney, Agent, or Firm*—Lowe, Price, LeBlanc & Becker

[57] ABSTRACT

A method for suppressing the capacity of a mammal to mount an immune response which would be caused by the administration of one or more biologically active foreign proteins, comprising the administration of an immunosuppressively effective amount of a tolerogen corresponding to said foreign protein or proteins, said administration being performed prior to the administration of said protein or proteins.

7 Claims, No Drawings

METHOD FOR THE SUPPRESSION OF AN IMMUNE RESPONSE

This application is a continuation of application Ser. No. 07/444,263 filed Dec. 1, 1989 now abandoned.

FIELD OF THE INVENTION

The present invention relates to a method for suppressing the capacity of a mammal to mount an immune response caused by the administration of one or more foreign proteins. Foreign proteins, or their derivatives, have often therapeutic properties and are, therefore, administered to patients suffering from certain diseases. However, as discussed later, the immunogenicity of the said foreign proteins, or of their derivatives, may vitiate the treatment and hence this invention provides an improved method for the treatment of such diseases.

Generally the term antigen refers to a substance capable of eliciting an immune response and ordinarily this is also the substance used for detection of the corresponding antibodies by one of the many in vitro and in vivo immunological procedures available for the demonstration of antigen-antibody interactions. Similarly, the term allergen is used to denote an antigen having the capacity to induce and combine with reaginic antibodies which are responsible for common allergies; however, this latter definition does not exclude the possibility that allergens may also induce antibodies other than reaginic antibodies, which include primarily immunoglobulins of the IgE class. As used herein, the term antigenicity is defined as the ability of an antigen or allergen to combine in vitro with the corresponding antibodies; the term allergenicity or skin activity is defined as the ability of an allergen to combine in vivo with homologous reaginic antibodies thereby triggering systemic anaphylaxis or local skin reactions, the latter reactions being performed as direct skin tests or as passive cutaneous anaphylactic (PCA) reactions; and the term immunogenicity in a limited sense is the capacity of an antigen or allergen or of their derivatives produced in vitro or processed in vivo to induce the corresponding specific antibody response.

In relation to this invention, tolerogens are defined as immunosuppressive covalent conjugates between an antigenic protein and a water-soluble polymer (see e.g. Sehon, A. H.,; In "Progress in Allergy" (K. Ishizaka, ed.) Vol. 32 (1982) pp. 161-202, Karger, Basel; and U.S. Pat. No. 4,261,973). In the present context and claims the term tolerogen thus refers to a protein-polymer conjugate which is immunosuppressive in an immunologically specific manner with respect to the antigen which is incorporated into the tolerogenic conjugate irrespective of the immunoglobulin class which is affected; furthermore, the tolerogen may comprise a conjugate of an essentially nonimmunogenic polymer and a biologically active derivative of the protein, the latter having been synthesized by grafting onto it synthetic or natural molecules possessing therapeutic properties prior to or after coupling to the said polymer.

The therapeutic administration of a foreign protein induces in general an immune response leaning to the formation of antibodies of different immunoglobulin classes. Hence, on repeated administration, the protein may form complexes in vivo with such antibodies leading to a poor therapeutic effect by virtue of its being sequestered and neutralized by the antibodies, or to anaphylactic reactions by combination with reaginic antibodies, or to other untoward conditions, i.e. immune complex diseases due to the deposition of antibody-antigen complexes in vital tissues and organs.

THE OBJECTIVES OF THE INVENTION

The therapeutic procedures mentioned above which involve the administration by itself of a foreign protein or of its biologically active products Goes have certain disadvantages and limitations. The objectives of the present invention aim at overcoming the above mentioned complications by suppressing the production of antibodies to the foreign therapeutic protein and of thus ensuring the efficacy of a therapy by the administration of reduced doses of therapeutically active proteins and by minimizing the risk of inducing anaphylactic reactions or immune complex diseases. Thus, the main objective of the invention aims at suppressing substantially an immune response which would undermine the therapeutic efficiency of a biologically active protein and which may also cause untoward physiological reactions (e.g. anaphylaxis and/or immune complex diseases).

These objectives are accomplished by a method, wherein an immunosuppressively effective amount of a tolerogen incorporating a foreign protein or its active derivative(s) is administered to the mammal prior to the administration of the foreign protein or its biologically active derivative(s). The invention is preferably applied to individuals who have not received a prior treatment with the foreign protein, i.e. to unsensitized individuals.

The invention will provide improved methods for therapy of different human diseases which can be ameliorated or eliminated by the administration of foreign proteins or their therapeutic derivatives synthesized by covalent or noncovalent attachment of natural or synthetic biological molecules such as for example (i) murine or rat monoclonal antibodies to human T-cells which have been used to suppress transplant rejection (Colvin, R. B. et al.; Fed. Proc. 41 (1982) p. 363, Abstr. 554) or as "miracle bullets" for the destruction of tumors (Froese, G. et al.; Immunology 45 (1982) p. 303-12, and Immunoiogical Reviews 62 (1982), Ed. G. Möller, Munksgaard, Copenhagen), (ii) enzymes, such as superoxide dismutase (Kelly, K. et al.; Cdn. J. of Physiol. Pharmacol., 609 (1982) p. 1374-81) or L-asparaginase (Uren, Jr. et al.; Canc. Research 39 (1979) p. 1927-33), or (iii) natural or synthetic hormones.

In the presently best developed and therefore also currently best preferred mode of the invention, the tolerogen is a covalent conjugate between monomethoxypolyethylene glycol (mPEG) with molecular weight in the range of 4,500-10,000 daltons and a model foreign protein such as ovalbumin (OA). According to this modality, tolerogens of appropriate composition (i.e. consisting of the protein and an optimal number of mPEG chains attached to it covalently) substantially suppress the formation of antibodies of different classes (i.e. IgE, IgG and IgM) which are directed specifically against the protein per se and/or against other foreign molecules grafted covalently or noncovalently onto the protein. The latter case is exemplified by the covalent derivative of OA with a number of 2,4-dinitrophenyl groups (DNP), i.e. OA-DNP$_n$, where n represents the average number of DNP groups coupled per one OA molecule.

The Tolerogen Employed

As water-soluble polymers to be used for the preparation of a tolerogen, polyethylene glycols, having molecular weights in the range of 2,000 to 35,000, have proved to be effective. Polyethylene glycols in this context also include physiologically acceptable derivatives thereof, such as mono-alkyl ethers, preferably the monomethyl ether, whereby the remaining terminal hydroxyl groups of the molecules are conveniently used for coupling to the protein.

Also other water-soluble polymers (macromolecules) may be used, such as polyvinylalcohols, polyvinylpyrrolidones, polyacrylamides and homo- as well as heteropolymers of amino acids, polysaccharides (e.g. pullulan, inulin, dextran and carboxymethyl cellulose) or physiologically acceptable derivatives of these polymers.

For the covalent coupling of such polymers to the antigen molecules, chemical methods normally used for coupling of biologically active materials to polymers may be used. Such methods include coupling by means of mixed anhydride, cyanuric chloride, isothiocyanate, reaction between SH derivatives and $CH_2I$ derivatives of the reacting molecules. However, it is quite obvious to the workers skilled in the art that other appropriate chemical methods may be used to lead to the production of conjugates of desired compositions.

The coupling reaction is made between active groups in the antigen molecules and in the polymer molecules. If necessary such groups may have to be introduced into said molecules before the coupling reaction. Such active groups are for example $-NH_2$, $-NCS$, $-SH$, $-OH$, $-Ch_2I$ and $-COOH$ and they may be introduced according to well-known methods, if not already present in the molecules used for the production of tolerogenic conjugates.

In order to minimize the liberation in vivo of the immunogenic and/or allergenic constituent(s) of the tolerogenic conjugates and to maximize their effectiveness at a low dose, it is desirable that the covalent link between the water-soluble polymer and protein or its active derivative(s) should be as stable as possible under physiological conditions.

The coupling of the polymer onto the antigenic protein must, as mentioned above, have been carried out to such an extent that the conjugate is rendered tolerogenic, as well as substantially non-allergenic and substantially non-immunogenic. In other words the tolerogens may posses a certain degree of immunogenicity as long as they do not induce the formation of antibodies which may cause unacceptable adverse reactions, and accordingly a certain degree of immunogenicity may be allowed depending on how serious is the disease which is being treated. To achieve tolerogenicity, the degree of substitution—which is defined as the number of polymer molecules coupled per protein antigen molecule—varies from one protein to another depending on the polymer in question and on the molecular weight of a polymer of a given type. Therefore, it is obvious that for the preparation of a tolerogenic conjugate of a given antigen it is essential to synthesize a series of conjugates with different degrees of substitution and then establish the special range wherein the above mentioned requirements are fulfilled. Too low a degree of substitution may result in allergenic and immunogenic conjugates and too high a degree of substitution may result in conjugates which are not tolerogenic.

In view of the finely tuned homeostatic balance of the immune response, which may be easily perturbed either upwards or downwards by the administration of a given antigen depending on its dose, state of aggregation and route of administration, as well as the presence or absence of adjuvants, it is critical that—when practicing the invention for treatment of appropriate disease conditions—the tolerogenic conjugates be administered in such a manner as to lead to the downregulation of the immune response with respect to one or more classes of immunoglobulins directed against the unconjugated biologically active protein. Hence, in practicing this invention for treatment of appropriate diseases, the tolerogenic conjugates are to be injected in absence of adjuvants since the adjuvants may counteract their suppressogenic effects. However, the inclusion of adjuvants along with the unconjugated immunogenic protein in the examples given below was justified so as to stimulate in experimental animals the enhanced production of antibodies in a relatively short time and to test the capacity of the tolerogenic conjugates to suppress the immune response in these animals even under these extreme conditions which are particularly favorable for enhancing the response.

The Foreign Protein

In the claims and in the specifications, proteins and polypeptides are used synonymously. In the present context and claims the term foreign protein refers to a protein or protein derivative (fragments included) which are substantially immunogenic in the animal to be treated.

The foreign protein, or its derivatives synthesized by grafting onto it biologically or pharmacologically active molecules (e.g. "miracle bullets"); to be used according to one aspect of the invention should be therapeutically effective. Many such proteins are known per se as indicated above. The effective doses (amounts) and formulations commonly used are also known per se and may be applied to the present invention, although the invention potentially may employ reduced or increased doses. For the reasons stated above, immunologic adjuvants should not be used. In principle, both the biologically active foreign proteins or their derivatives, as well as the corresponding tolerogenic conjugates, may be administered parenterally in a soluble form in isotonic solution and after removal of aggregates by centrifugation.

Time Intervals for the Administration

The protocol followed according to the invention comprises the administration initially of an immunosuppressively effective dose (amount) of tolerogen, which is given prior to the administration of the therapeutically active protein or its product. If necessary, this dose may be portioned and given on repeated occasions. The immunosuppressive dose as well as the time period, over which it is given, vary from tolerogen to tolerogen as well as from protein to protein. According to the principles outlined in the examples, the practitioner skilled in the art can determine these variables. However, the immunosuppressive dose refers to the amount of tolerogen required to substantially reduce the immunogenicity of the protein or of its derivative(s) to be administered. According to one mode of the invention, further doses of the tolerogen may be given in conjunction with the protein or its derivative(s), i.e. after the primary administration of the tolerogen. This mode may represent one way of sustaining the suppression and may offer a more efficient therapeutic regimen for the disease condition for which the treatment has been designed.

The invention will now be illustrated by some non-limiting examples wherein OA and its tolerogenic mPEG derivatives have been applied as model substances to test the usefulness of the proposed immunosuppressive treatment of a well-established animal model commonly utilized in the field of immunology. The conjugates will be designated as OA-mPEG$_n$ where n represents the average degree of substitution.

EXAMPLE 1

Preparation of OA-mPEG Conjugates having Different Degrees of Substitution

The conjugates used in the experiments given below have been prepared by coupling mPEG molecules to OA essentially according to the procedure described by Abuckowski et al (J. Biol. Chem. 252, 3518, 1977 utilizing cyanuric chloride as the coupling agent. To begin with, the "active intermediate" consisting of an mPEG molecule attached to cyanuric chloride, which is illustrated by the formula given below, was prepared.

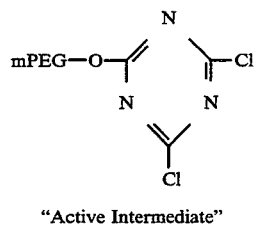

"Active Intermediate"

It was found that the most important condition of this reaction was that all reagents be completely anhydrous and that the reaction mixture be protected from atmospheric moisture because of its high susceptibility to hydrolysis. Among various methods used for the synthesis of the "active intermediate", the example given below illustrates the general procedure.

Monomethoxypolyethyleneglycol (2.5 g, mol wt 5590, Union Carbide) was dissolved with warming in anhydrous benzene (40 ml) and a portion of the benzene (20 was removed by distillation to azeotrope off any water in the polymer. Cyanuric chloride [(CNCl)$_3$, 0.83 Aldrich, recrystallized from benzene] was added under nitrogen followed by potassium carbonate (0.5 g, anhydrous powdered) and the mixture stirred at zoom temperature for 15 hours, The mixture was then filtered under dry nitrogen and the filtrate mixed with anhydrous petroleum ether (ca 50 ml, b.pt. 30°-60° C.) in order to precipitate the polymer. The polymer was separated by filtration under nitrogen, dissolved in benzene (20 ml) and reprecipitated with petroleum ether. This process was repeated seven times to insure that the polymer was free of any residual cyanuric chloride. The active intermediate was finally dissolved in benzene, the solution frozen and the benzene sublimed away under high vacuum to leave a fine white powder.

Elemental analysis of the intermediate confirmed that it contained 2 chlorine atoms. The intermediate, corresponding to $C_{256.3}H_{307.7}O_{127.2}N_3Cl_2$ with an average molecular weight of 5,738 daltons would have a theoretical composition in percentages of C, 53.65; h, 8.92; N, 0.73; Cl, 1.24; which agrees with its determined composition of C, 53.51; H, 8.98; N, 0.77; Cl, 1.08.

The chloride content of the intermediate was also determined by hydrolysis and titration of the chloride released with silver nitrate. Thus, the activated intermediate (120 mg) was dissolved in water (10 ml) and the pH adjusted to 10 with dilute sodium hydroxide. After heating at 90° C. for two hours, the solution was cooled and the chloride titrated with silver nitrate (0.001N), using a chloride ion selective electrode to indicate the endpoint. The chloride content of the activated intermediate was found to be 2.1, consistent with the structure shown above.

The OA [40 mg, purified by chromatography on Ultrogel® AcA-54 (LKB, Bromma, Sweden)] was dissolved in sodium tetraborate buffer (4 ml, 0.1M, pH 9.2) and the activated mPEG added to the solution at 4° C. The amount of activated mPEG was varied to prepare conjugates of differing degrees of polymer substitution. Mole ratios (mPEG/OA) used to prepare specific conjugates are given in Table 1. The polymer-protein mixture was stirred for one half hour at 4° C. and then one-half hour at room temperature. The reaction mixture was desalted by either dialyzing for four days against running distilled water or by passing through a column of Sephadex® G-25 (Pharmacia Fine Chemicals AB, Uppsala, Sweden).

A DEAE-cellulose or DEAE-Sephacryl® (Pharmacia Fine Chemicals AB, Uppsala, Sweden) column (5 cm by 30 cm) was equilibrated with phosphate buffer (0.008M, pH 7.7). The salt free OA conjugates were applied in water and the free (unbound) mPEG washed through the column with the pH 7.7 buffer. Free mPEG was detected on thin layer chromatography [Camag (Kieselgel DSF-5, Terochem Lab Ltd, Alberta) eluant 3:1 chloroform/methanol] using iodine vapour for development. After removal of the free PEG from the ion-exchange column, sodium acetate buffer (0.05M, pH 4.0) was used to elute the conjugate. The conjugate fractions were dialyzed and lyophilized to give the dry conjugates.

TABLE 1

| Preparation of OA-mPEG$_n$ Conjugates | | | |
|---|---|---|---|
| Conjugates[a] | Preparation ratio[b] | % mPEG[c,e] | % OA[d,e] |
| OA-mPEG$_{3.2}$ | 10:1 | 26 | 70 |
| OA-mPEG$_{6.6}$ | 25:1 | 36 | 47 |
| OA-mPEG$_{7.6}$ | 25:1 | 42 | 47 |
| OA-mPEG$_{10.6}$ | 50:1 | 51 | 41 |
| OA-mPEG$_{11.9}$ | 50:1 | 52.4 | 38 |

[a]The degree of substitution, n, is calculated by the formula
$$\frac{\% \text{ mPEG}}{\% \text{ OA}} \times \frac{\text{mol wt OA}}{\text{mol wt mPEG}}$$
[b]Mole ratio mPEG:OA based on a molecular weight of 5.740 for mPEG-dichlorocyanurate and 44.460 daltons for OA.
[c]The percentages of mPEG by weight were determined by nuclear magnetic resonance (NMR).
[d]The percentages of protein by weight were determined by the biuret method.
[e]The total compositions of the conjugates, as calculated from the NMR and biuret analysis, are only of the order of 90% of the samples by weight; the difference of the order of 10% is attributed to moisture absorbed by the conjugates and/or to small amounts of DEAE-cellulose leaching from the column.

EXAMPLE 2

Determination of the Immunosuppressive Effect on the IgE Response of Different OA-mPEG$_n$ Conjugates The results of these experiments demonstrate the stringent dependency of the suppressogenicity of mPEG conjugates on their molecular composition. Thus, whereas treatment of groups of four (B6D2)F1 mice each with 50 μg of OA-mPEG$_{3.2}$, or OA-mPEG$_{6.6}$, or OA-mPEG$_{7.6}$ one day prior to intraperitoneal immunization with the sensitizing dose, consisting of 1 μg of OA and 1 mg Al(OH)$_3$, led to essentially complete (99–100%) abrogation of the primary anti-OA IgE response, as measured on day 14 after immunization by PCA in hooded rats, the more substituted conjugates, i.e. OA-mPEG$_{10.6}$ and OA-mPEG$_{11.9}$, inhibited the anti-OA IgE response, respectively, only to the extent of 94% and 50%. In this and the following examples, the weights of the conjugates given correspond to their protein content.

EXAMPLE 3

Long Lasting Suppression of the IgE Response Protein-mPEG Conjugates in Contrast to a Transient Suppressive Effect of Unconjugated Protein It is to be noted that even unmodified OA was capable of downregulating the primary IgE response in relation to the response of control mice which had received PBS instead of OA or conjugates. In this experiment three groups of four (B6D2)F1 mice each received phosphate buffered saline, or 50 μg of OAm-$PEG_{4.5}$ or 50 μg of OA. All animals were bled on day 10, 14, 21, 27, 35, 42 and 49 and their IgE titers were determined by PCA in hooded rats. As illustrated in Table 2, it is important to point out that whereas the suppressogenic effect of OA-mPEG conjugates was long-lasting, the downregulating effect of free OA was of short duration and, in actual fact, its administration predisposed the animals to an anamnestic response which reached, after booster immunization (administered on day 28), IgE antibody levels equivalent to those of control animals which had received PBS and the two sensitizing doses of one antigen. The results given in Table 2 clearly demonstrate that a tolerogenic conjugate injected prior to repeated administration of the corresponding free protein essentially abrogated the immune response.

TABLE 2

Effect of Arhninistering 50 μg of OA-$mPEG_{4.5}$ or of free OA one day prior to immunization

| Day of bleeding after primary immunization | PCA titers for groups of mice treated with PBS | OA | OA-$mPEG_{4.5}$ |
|---|---|---|---|
| 10 | 5,120 | 40 | <4 |
| 14 | 1,940 | 40 | <4 |
| 21 | 1,280 | 40 | <4 |
| 27 | 640 | 40 | <4 |
| 35 | 1,920 | 1,920 | 160 |
| 42 | 2,560 | 1,280 | 160 |
| 49 | 5,120 | N.D.* | 160 |

On day 28 all three groups received a booster dose of the sensitizing OA preparation.
*N.D. = not determined

EXAMPLE 4

The Effect of Different Doses of the Tolerogen on the IgE Response

Each OA-mPEG conjugate was injected into groups of 4 mice each at the four doses of 10 μg, 50 μg, 150 μg and 600 μg. The control group of mice received PBS as placebo.

Treatment with different conjugates at doses of 10 μg and 50 μg per mouse revealed marked differences in their suppressogenic capacity. It is also to be noted that at a dose of 150 μg, all conjugates were highly suppressive and at 600 μg all the compounds tested suppressed completely the IgE response.

EXAMPLE 5

The Effect of OA-$mPEG_{10}$ on the Suppression or IgM, IgG and IgE Plaque Forming Cells (PFC) in Spleen and Lymph Nodes One mg of OA-$mPEG_{10}$ (containing 10 mPEG groups with an average mol wt of 10,000 daltons which were coupled per OA molecule by the succinic anhydride method [Wie, S. I. et al., lnt. Archs. Allergy appl. Immun. 6.4., 84, (1981] or PBS was administered intraperitoneally to each group of four (B6D2)F1 mice each one day prior to immunization with 1 μg $DNP_3$-OA in 1 mg $Al(OH)3$. On several days thereafter the spleen, as well as the mesenteric, parathymic and linguinal lymph nodes were removed and assayed for IgM, IgG and IgE anti-DNP PFC (Rector, E. S. et al., Eur. J. lmmunol. 10 (1980) p. 944–49). in Table 3 are given the numbers of PFC in the above tissues 10 days after immunization; from these data it is evident that treatment with this tolerogen markedly reduced the number or IgM, IgE and IgG PFC in all tissues examined. Therefore, these results support the claim that the tolerogens shut off the immune response rather than neutralize circulating antibodies.

TABLE 3

The effect of OA-$mPEG_{10}$ on the suppression of IgM, IgG and IgE plaque forming cells (PFC) in spleen and lymph nodes

| Antibody Class | Treatment | Anti-DNP PFC per $10^8$ cells from different tissues* Spleen | Parathymic Nodes | Mesenteric Nodes | Inguinal Nodes |
|---|---|---|---|---|---|
| IgM | PBS | 2,150 | 2,950 | Nd | Nd** |
| | OA-mPEG | 900 | 200 | Nd | Nd |
| IgG | PBS | 15,350 | 78,550 | 5,000 | Nd |
| | OA-mPEG | Nd | 1,300 | Nd | Nd |
| IgE | PBS | 10,410 | 16,350 | 11,140 | 300 |
| | OA-mPEG | 550 | 950 | 400 | Nd |

*Each tissue sampling represents a pool from 4 mice
**Nd—undetected

As discussed above and described in U.S. Pat. No. 4,261,973 of Apr. 14, 1981; (Inventors: W. Y. Lee and A. Sehon), an antigen (Ag) may be converted to a tolerogen by coupling onto it an optimal number of molecules of monomethoxypolyethylene glycol (mPEG). Thus, injection of tolerogenic mPEG conjugates of a variety of Ags into mice and rats, prior to the administration of the corresponding unmodified Ags, leads to the abrogation of the capacity of the animals to mount humoral antibody responses to the appropriate Ags. The mPEG conjugate of a given Ag is represented by the formula Ag(mPEG)n; the subscript "n" represents the average degree of conjugation and corresponds to the average number of mPEG molecules coupled covalently onto the Ag. In the experiments to be reported here, the molecular weight of mPEG preparations used was 6,000 Da. For the synthesis of an effective tolerogen, the "n" value must be within the synthesis of an effective tolerogen, the "n" value must be within an optimal range, i.e. too low a degree of conjugation does not result in total loss of immunogenicity of the Ag and too high a degree of conjugation leads to immunologically inert products.

One of the greatest challenges of modern immunology is to devise strategies for the selective abrogation of harmful immune responses, as is the case in IgE-mediated allergies and auto-immune diseases. The ability to induce specific immunological suppression is also of particular importance for the development of novel therapies which depend on the administration of specially designed natural or synthetic, complete or fractional xenogeneic monoclonal antibodies (xMabs) by themselves, or in the form of conjugates with therapeutic agents, such as tumoricidal or viricidal drugs, bacterial or plant toxins, e.g. chain A of ricin (RAC). These conjugates will be referred to hereafter as immunotoxins (ITX). For example, for the therapeutic destruction of cancer cells, "magic bullets" consisting of such ITX have been used but with limited success, because the effectiveness of xMabs or of ITX is undermined by their inherent immunogenicity; it is to be stressed that the immunogenicity of RAC is even higher than that of xMabs. As a result of this inherent immunogenicity, the recipients produce antibodies against the epitopes of ITX, which combine with the epitopes of ITX. As a result of this interception, the "magic bullets" are prevented from reaching their targets. Therefore, the importance of the developing methods for suppressing the patient's immune response selectively to xMabs or ITX cannot be overemphasized. As supported by the results reported below, it is envisaged that these complications can be overcome not only by the use of tolerogenic mPEG derivatives of ITX but, more importantly, by pretreatment of the patient with tolerogenic mPEG conjugates of the XMabs alone.

THE PRESENT INVENTION

The model system used for this invention consisted of monoclonal (myeloma) human IgG (HIgG) as the xMabs and the corresponding tolerogenic HIgG(mPEG)phd n conjugates, utilizing different strains of inbred mice. Pretreatment of mice with HIgG(mPEG)$_n$ resulted in significant suppression (>95%) of their antibody responses to HIgG for at least 530 days, in spite of multiple injections of the immunogenic unmodified HIgG. (Details of the methods used and of the results obtained are given in a publication by P. K. Maiti, G. M. Lang and A. H. Sehon, International Journal of Cancer: Supplement 3, 17-22, 1988).

The present invention which is based on the above data but which is a totally original discovery—pertains to a method of suppression of the immune response to a given Ag (e.g., DNP$_{23}$-KLH) which is administered in the form of a conjugate with an unrelated Ag (e.g., DNP$_{23}$-KLH-HIgG), on condition that the recipient animal had been pretolerized by prior treatment with a tolerogenic mPEG conjugate of the said unrelated Ag [i.e., (HIgG)mPEG$_{25}$]. In the example reported here, the immunogenic dinitrophenylated keyhole limpet haemocynin(DNP$_{23}$-KLH) plays the role of the second Ag, HIgG plays the role of the first Ag (i.e., unrelated Ag), HIgG(mPEG)$_{25}$ is the tolerogenic mPEG derivative of the unrelated Ag, and DNP$_{23}$-KLH-HIgG is the conjugate of both Ags. The protocol of the experiment and the results are illustrated in Table 4.

Briefly, (i) the results involving groups 1 and 2 of mice demonstrate that administration of HIgG(mPEG) suppresses radically the immune response of the recipient to HIgG as well as to DNP, i.e., corresponding anti-HIgG and anti-DNP antibodies are substantially decreased in animals pretreated with HIgG(mPEG)$_{25}$ (in this case the DNP plays simply the role of a hapten attached to the HIgG carrier protein, the latter being also incorporated into the tolerogenic conjugate);

(ii) the results involving groups 3, 4, 5 and 6 demonstrate that (a) animals pretolerized with HIgG(mPEG)$_{25}$ are essentially incapable of mounting an immune response not only to HIgG but also to DNP and KLH when the corresponding antigen (DNS$_{23}$-KIH) is coupled covalently to HigG and injected in the form of DNP$_{23}$-KLH-HIgG (groups 3 and 6), and (b) by contrast, when DNP$_{23}$-KLH is administered in the presence of HIgG, but without having been coupled to the latter, the immune system of the animals pretolerized with HIgG(mPEG)$_{25}$ responds in a normal manner to the epitopes of both DNP and KLH, but remains silent to HIgG (groups 5 and 6).

The results reported herein are totally novel and unexpected in the field of Immunology. In other words, these results are deemed to have established a new principle which may have far-reaching importance in developing new therapeutic modalities which require the induction of tolerance to a given therapeutically beneficial Ag prior to its administration.

In this invention, it is claimed and substantiated by the results presented in Table 4 that "prior suppression of immunity with a tolerogenic derivative of a given antigen abrogates the immune response to a second antigen, on condition that the latter is administered as a covalent conjugate with the first antigen".

TABLE 4

| | CARRIER-SPECIFIC SUPPRESSION OF ANTIBODY RESPONSES IN MICE PRETREATED WITH TOLEROGENIC CARRIER-mPEG CONJUGATES | | | | |
|---|---|---|---|---|---|
| | | | IgGl ELISA Titres on Day 70 | | |
| Groups | Treatment[a] | Antigen | anti-DNP | anti-HIgG | anti-KLH |
| 1 | PBS | DNP$_7$-HIgG | 15,225 ± 1426 | 32,333 ± 6741 | N/A |
| 2 | HIgG(mPEG)$_{25}$ | " | 3,413 ± 972 | 580 ± 212 | N/A |
| 3 | PBS | DNP$_{23}$-KLH-HIgG | 4,263 ± 1688 | 12,667 ± 5780 | 6,800 ± 2150 |
| 4 | HIgG(mPEG)$_{25}$ | " | 1,072 ± 424 | 603 ± 113 | 243 ± 120 |
| 5 | PBS | DNP$_{23}$-KLH + HIgG | 7,466 ± 1790 | 20,625 ± 4220 | 25,300 ± 5490 |
| 6 | HIgG(mPEG)$_{25}$ | " | 9,438 ± 657 | 316 ± 98 | 30,950 ± 1240 |

[a]Test mice were given to i.v. injections of 100 ug each of tolerogenic HIgG(mPEG)$_{25}$ on days 0 and 14; control mice received PBS in lieu of the mPEG conjugate. All mice received three i.p. injections of 100 ug of the antigens indicated in column 2 on days 28, 42, 56.

The present invention is based on the unexpected discovery that pre-treatment of a recipient with a tolerogen suppresses the immunoresponse not only to the antigen use in the tolerogen but also to a conjugate of that antigen and a second antigenic moiety.

Accordingly, there is provided a kit comprising, as a first component, a first antigen in the form of a tolerogenic compound and, as a second component, a conjugate of the first antigen and a second antigen.

Also provided is the use of a first antigen in the manufacture both of a tolerogenic compound and of a conjugate with a second antigen for use in sequential administration to a recipient.

Suitably, the first antigen is a recognition factor for binding to a target within the recipient. Such recognition factors include antibodies, particularly xMabs. The second antigen is generally a biologically active agent, possibly having therapeutic use. One suitable combination is an anti-monoclonal antibody and the chain A of ricin. In this way the invention can be used in suppressing a patient's immune response selectively to xMabs or ITX.

Preferably mPEG is used to conjugate the first antigen to form the tolerogen. For the synthesis of an effective tolerogen, the "n" value must be within optimal range, i.e., too low a degree of conjugation does not result in total loss of immunogenicity of the Ag and too high a degree of conjugation leads to immunologically inert products.

An embodiment of the present invention is now described by way of example.

The article by Maiti et al in International Journal of Cancer: Supplement 3, 17–22, 1988 discloses a model system for testing tolerogens of monoclonal (myeloma) human IgG. (HIgG) as the xMabs conjugated with mPEG which utilizes different strains of inbred mice. In this article, it was found that pre-treatment of mice with $HIgG(mPEG)_n$ resulted in significant suppression ($>95\%$) of their antibody responses to HIgG for at least 530 days, in spite of multiple injections of the immunogenic unmodified HIgG.

In the present example the molecular weight of mPEG preparations used was 6,000 Da. The tolerogen used was $HIgG(mPEG)_{25}$ and the conjugate was HIgG covalently bonded to the immunogenic dinitrophenylated keyhole limpet haemocynin ($DNP_{23}$-KLH). The antigens HIgG and $DNP_{23}$-KLH are unrelated antigenically.

The experiment was carried out in the following way:

Test mice were given two intravenous injections of 100 μg each of tolerogenic $HIgG(mPEG)_{25}$ on days 0 and 14; control mice received PBS in lieu of the mPEG conjugate. All mice received three i.p. injections of 100 μg of the antigens indicated in the second column of Table 4 on days 28, 42, 56.

The results involving groups 1 and 2 of mice demonstrate that administration of $HIgG(mPE6)_{25}$ suppresses radically the immune response of the recipient to HIgG as well as to $DNP_7$-HIgG. The corresponding anti-HIgG and anti-DNP antibodies are substantially decreased in animals pre-treated with $HIgG(mPE6)_{25}$. In this case the DNP plays simply the role of a hapten attached to the HIgG carrier protein, the latter being also incorporated into the tolerogenic conjugate.

The results involving groups 3 and 4 demonstrate that animals pre-tolerized with $HIgG(mPEG)_{25}$ are essentially incapable of mounting an immune response not only to HIgG but also to DNP and KLH when the corresponding antigen, $DHP_{23}$-KLH is coupled to HIgG and injected in the form of $DNP_{23}$-KLH-HIgG.

The results involving groups 5 and 6 demonstrate that animals pre-tolerized with $HIgG(mPEG)_{25}$, do not mount an immune response to HIgG. However, when $DNP_{23}$-KLH is administered in the presence of HIgG but without having been coupled thereto, the immune system of the animals responds in a normal manner to the epitopes of both DNP and KLH.

We claim:

1. A method of suppressing a mammal's antibody-mediated immune response to a second antigenic polypeptide, or biologically active fragments thereof, the method comprising
   (a) selecting a mammal which is unsensitized to a first antigenic polypeptide or antigenically active fragments thereof,
   (b) administering an immunosuppressive amount of a tolerogenic conjugate comprising said first antigenic polypeptide, or antigenically active fragments thereof, covalently bound to a physiologically-acceptable, monovalent, water-soluble polymer, and subsequently
   (c) administering to said mammal a conjugate comprising said first antigenic polypeptide, or biologically active fragments thereof covalently bound to said second antigenic polypeptide, or biologically active fragments thereof, said conjugate administered in an amount effective to deliver a biologically-effective amount to suppress said mammal's immune response to said second antigenic polypeptide, or biologically active fragments thereof;
   (d) wherein administration of said tolergenic conjugate suppresses the capacity of said mammal to mount a humoral antibody response to said first antigenic polypeptide so that when said first antigenic polypeptide is conjugated to said second antigenic polypeptide said mammal's antibody-mediated immune response to said biologically active second antigenic polypeptide is suppressed.

2. The method of claim 1, wherein said second antigenic polypeptide is selected from the group consisting of toxins, tumoricidal drugs, viricidal drugs, bacterial toxins, plant toxins, xenogeneic antibodies, and combinations thereof.

3. The method of claim 1, wherein said first antigenic peptide of said tolergenic conjugate is selected from the group consisting of xenogeneic monoclonal and polyclonal antibodies.

4. The method of claim 1, wherein said physiologically-acceptable, monovalent, water-soluble polymer is selected from the group consisting of poly(alkyleneglycols), poly(vinylalcohols), poly(vinylpyrolidones), poly(acrylamides), homo- and heteropolymers of amino acids, poly(saccharides), physiologically-acceptable derivatives thereof and mixtures and combinations thereof.

5. The method of claim 4, wherein said polymer is a poly(alkylene glycol).

6. The method of claim 5, wherein said poly(alkylene glycol) is monomethoxy poly(ethylene glycol).

7. The method of claim 1, further comprising repeating step (a) simultaneously with step (b).

* * * * *